United States Patent
Heckerman et al.

(10) Patent No.: US 6,257,887 B1
(45) Date of Patent: Jul. 10, 2001

(54) DENTAL HAND INSTRUMENT (75) Inventors: Brad B. Heckerman, Florence; Russ Jenkins, Ronan; Dennis Meuchels; Jeff Smithers, both of Missoula, all of MT (US)

(73) Assignee: American Eagle Instruments, Inc., Missoula, MT (US)

( * ) Notice: Subject to any disclaimer, the term of this patent is extended or adjusted under 35 U.S.C. 154(b) by 0 days.

(21) Appl. No.: 09/264,333

(22) Filed: Mar. 6, 1999

Related U.S. Application Data (63) Continuation-in-part of application No. 08/576,829, filed on Dec. 21, 1995, now abandoned.

(51) Int. Cl.[7] .................................................. A61C 3/00
(52) U.S. Cl. .......................................... 433/141; 433/143
(58) Field of Search .................................. 433/141, 143; 81/900

(56) References Cited

U.S. PATENT DOCUMENTS

| | | | |
|---|---|---|---|
| 1,209,789 | * 12/1916 | Wilson | 433/146 |
| 1,723,226 | 8/1929 | Withycombe | 433/141 |
| 2,163,993 | 6/1939 | Dufour et al. | 219/19 |
| 2,678,371 | 5/1954 | Andrew | 219/10.79 |
| 2,899,996 | 8/1959 | Stockman | 81/900 |
| 3,108,169 | 10/1963 | Keller | 219/10.49 |
| 4,024,617 | 5/1977 | McCormick | 29/156.63 |
| 4,501,943 | 2/1985 | Lund | 219/10.43 |
| 4,584,453 | 4/1986 | Fu | 219/10.43 |
| 4,759,713 | 7/1988 | Heiss et al. | 433/88 |
| 5,169,313 | 12/1992 | Kline | 433/143 |
| 5,208,443 | 5/1993 | McGaffigan | 219/505 |
| 5,359,911 | 11/1994 | Kruesi | 81/900 |
| 5,390,572 | 2/1995 | Gakhar et al. | 81/900 |
| 5,397,512 | 3/1995 | Sloane, Jr. et al. | 264/25 |

FOREIGN PATENT DOCUMENTS 2227412   8/1990   (GB).

* cited by examiner

*Primary Examiner*—John J. Wilson
(74) *Attorney, Agent, or Firm*—Dowrey & Associates (57) ABSTRACT

A dental hand instrument comprises an elongated handle formed of a thermosetting plastic and a metal working tip inserted into an end of the handle. The handle may be a multi-part assembly with replaceable working tip end sections. The handle has a bore provided in the end to accommodate a shank end of the tip. The handle and the tip are subjected to heat treatment to partially melt a portion of the thermosetting plastic adjacent to the shank end to bind the shank in solid plastic-to-metal contact along the shank end. The shank end of the tip is provided with a non slip surface that is encompassed and embedded in the thermosetting plastic so that the tip will not turn during use.

35 Claims, 5 Drawing Sheets

DENTAL HAND INSTRUMENT

CROSS REFERENCE TO RELATED APPLICATION

This Application is a Continuation-in-part of my application Ser. No. 08/576,829 filed Dec. 21, 1995.

BACKGROUND OF THE INVENTION

1. Field of the Invention

This invention relates to dental instruments and, more particularly, to hand held instruments having an elongated handle fitted with a working tip at one end or with working tips at both ends.

2. Brief Description of the Prior Art

Dental hand instruments are typically fabricated with elongated handles of stainless steel, chromed brass, or aluminum having a round or octagonal cross section of about ¼ inch diameter. Depending on the use of the instrument, the handle is fitted with a working tip of stainless steel, carbon steel, or other metal such as carbide at one end or with such working tips at both ends. Typical working tips include those employed in periodontics, hygienics and diagnostics such as curettes, scalers, probes, and explorers; in operatives such as angle formers, chisels, trimmers, excavators and carvers, and hatchet and hoe instruments; in endodontics such as dryers and spreaders and pluggers. A common factor in the use of instruments employing such tips is that the instruments must be gripped tightly and that the gripping fingers undergo repetitive movement while under substantial strain. Increasing symptoms of hand fatigue, cramping, strain and carpel tunnel syndrome are being reported with repetitive use of these standard instruments over extended periods of time, as is required in the daily practice of dentistry. The common practice of using latex gloves as protection may be a causative factor in the increase of these symptoms inasmuch as a hand held instrument is more difficult to manipulate with a gloved hand, perhaps requiring holding the instrument with greater force than would be required of a non-gloved hand. Use of latex gloves also reduces tactile sensitivity.

Increasing the diameter of the elongated handle from the standard ¼ to 5/16 inch would appear to be indicated. However, increasing the diameter increases the weight of the instrument, adding to hand fatigue. Moreover, the resulting increase in weight dampens the tactile sensitivity of the working tip, leading to increased hand fatigue.

Some attempts have been made to substitute elongated plastic handles for the standard stainless steel handle. However such attempts have resulted in numerous problems such as an incapability to withstand sterilization procedures, resulting in one-use throw-away instruments. This inefficiency becomes even more significant in the case of double ended instruments since discarding loses the benefit of the remaining serviceability of both tips. The ability to provide replaceable tips and to choose any particular combination of tips is also lost. Poorly designed handle surfaces has resulted in increased hand strain and fatigue, undesirable handle flexibility and dampening of the tactile sensitivity of the working tip.

SUMMARY OF THE INVENTION

It is a primary object of the present invention to provide a dental hand held instrument that satisfactorily solves the abovementioned difficulties experienced by prior instruments including the provision of a multi-piece handle allowing for replaceable tips, and mixing and matching any combination of working points while maintaining threaded areas free from debris and pathogens. It is another object to provide a dental hand instrument with a larger handle diameter that reduces hand strain and fatigue but that does not dampen the tactile sensitivity of the working tip. It is a further object to provide an elongated handle fabricated from a thermosetting plastic wherein the handle can be either molded in an injection molding process, or machined from rod stock. It is still another object of the present invention to provide a dental hand instrument wherein the elongated handle is fabricated from a thermosetting plastic and wherein stainless steel working tips are joined with the handle in a sanitary joint that will not harbor bacteria and other pathogens. These and other objects and advantages will become apparent from a consideration of the following description of a preferred embodiment of the invention.

In accordance with these objects, the invention provides a dental hand instrument comprising an elongated handle formed of a thermosetting plastic and a metal working tip inserted into an end of the handle. The handle has a bore provided in the end to accommodate a shank end of the tip. The handle and the tip are subjected to heat treatment to partially melt a portion of the thermosetting plastic adjacent to the shank end so as to firmly secure the tip in the handle and so as to bind the shank in solid plastic-to-metal contact along the shank end. The shank end of the tip is provided with a non slip surface that is encompassed and embedded in the thermosetting plastic so that the tip will not turn during use.

In one embodiment an improved replaceable tip instrument is provided utilizing a multi-piece handle including one or more replaceable tip sections with working tips fixed to the handle section in a manner according to the present invention. The independently exchangeable tips allow the user to mix and match any combination of working points and allows for replacement of worn or broken points as needed without losing the benefit of the remaining serviceability of opposing points in the case of double ended instruments. In addition, attachment of the handle section to the main handle portion allows for flush mounted in-line identification rings with improved wear and sterilization characteristics.

DESCRIPTION OF THE PREFERRED EMBODIMENT

Figure 1:
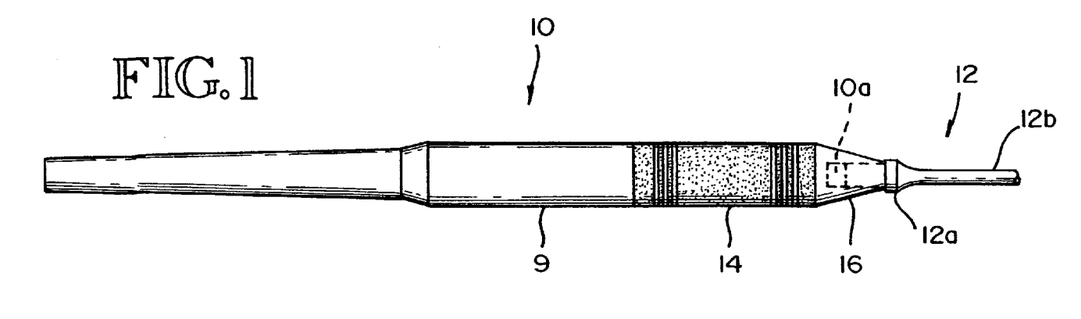
FIG. 1 is a side view of a dental hand instrument, with one working tip attached to its elongated handle, in accordance with the invention.
Figure 2:
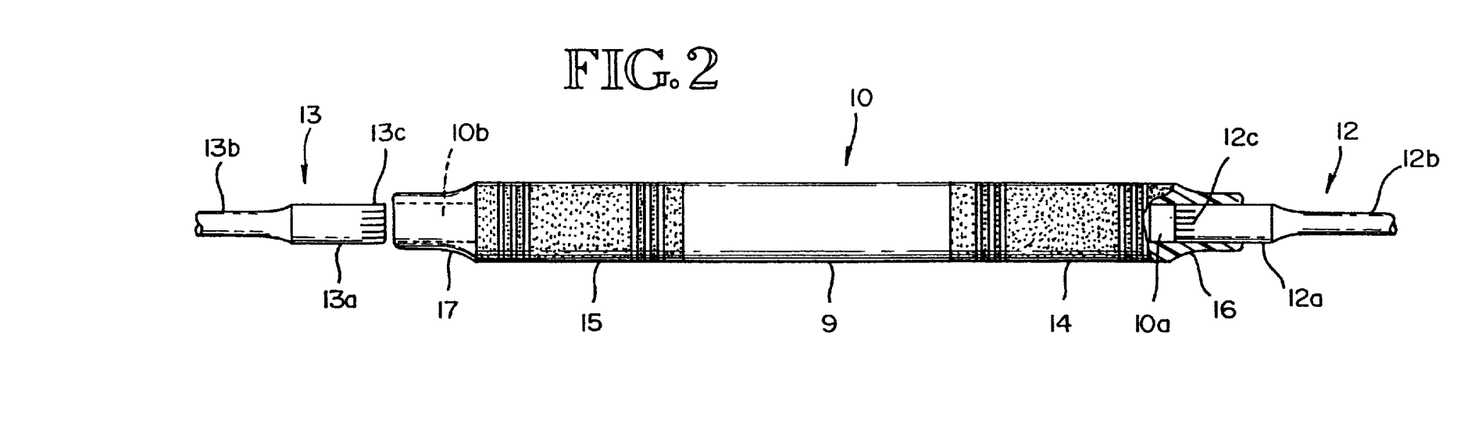
FIG. 2 is a side view of a handle for a dental hand instrument, designed to have two working tips attached thereto, with a left end working tip aligned for attachment, and with the right end working tip installed in accordance with the invention, a portion of the right end of the handle being shown in cross section to illustrate the joint between the working tip and the handle.

The dental hand instrument of the present invention comprises an elongated handle 10, fabricated of a thermosetting plastic, and at least one working tip 12. FIG. 1 illustrates the invention with one working tip 12 at one end of the handle, and FIG. 2 illustrates the invention with two working tips 12, 13, one at each end of the handle. The handle may be fabricated by various methods, such as by injection molding or by machining from rod stock, so long as the illustrated structures and features are achieved. The following discussion assumes that the handle is manufactured from a thermosetting plastic rod stock that has been extruded into the desire diameter, such as ⅜ inch round diameter.

In the case of an instrument having one working tip, such as is shown in FIG. 1, the instrument is provided with a working end having a finger gripping exterior surface 14 and a transition shoulder 16 between the surface 14 and the working tip 12. In the case of an instrument having two working tips, such as is shown in FIG. 2, the instrument is additionally provided with a second working end having a second finger gripping exterior surface 15 and a transition shoulder 17 between the surface 15 and the working tip 13. In either case, the working tip 12, 13 is provided with a shank end 12a or 13a and a working tip end 12b or 13b. (In the drawings, only so much of the working tip ends that extend from the shanks are shown, since the working tips ends can be of any configuration and are well known in the art.) The transition shoulders 16, 17 provide lands or rests for a user's fingers. The configuration of these lands or rests may be frusto-conical as seen in FIG. 1, or chamfered as seen in FIG. 2.

The center portion 9 of the handle, between the finger gripping surfaces 14, 15 in the case of FIG. 2, or toward the middle of the handle in the case of FIG. 1, is of the same general diameter as the finer gripping surfaces. Indicia identifying the instrument may be stamped into this portion, as by a roll press.

The shank end 12a or 13a of each working tip is inserted into the adjacent end of the handle as shown in the drawings, and protrudes from the handle and tapers into its working tip end 12b, 13b as shown. Also, in either case (such as FIG. 1 or FIG. 2), each working tip shank end 12a, 13a is provided with a non slip surface 12c or 13c in a region that will be enclosed by the handle. The butt of each working tip shank end 12a, 13a is preferably knurled to provide the non slip surface 12c, 13c.

Each working end of the handle, whether one or two, is provided with an axial bore 10a (FIG. 1), or 10a and 10b (FIG. 2) into which the working tip shank end 12a, 13a is inserted. The relative sizes of the bore diameter and the shank end diameter are such that there is a tight fit between the two, the bore diameter being slightly less than the shank end diameter. In general, forming each bore with a diameter about 0.002 inches less than the diameter of the corresponding shank end is sufficient.

The non slip surface 12c, 13c will have portions that extend above the surface of the shank end so that the interior side wall of the bore will be scored as the shank end is inserted into the bore. If the non slip surface is provided as a knurl, the bore interior side wall will be grooved by the tip shank insertion process. A straight knurl with a 160 diametrical pitch may be rolled into the butt of the shank end, about ⅛ inches long, with an outward protrusion beyond the surface of the shank end of about 0.004 inches (+ or −0.001 inches).

Figure 3:
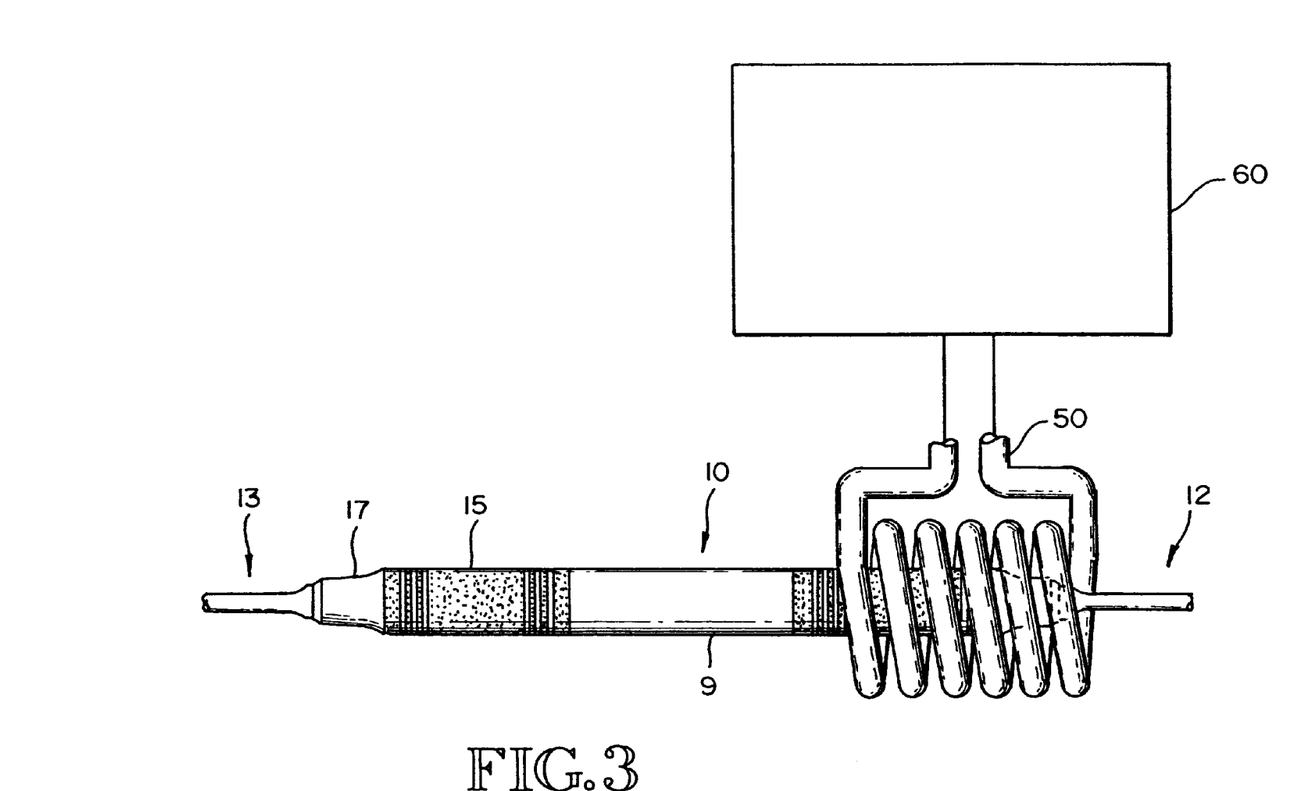
FIG. 3 is a side view of a dental hand instrument inserted into an induction heating coil to illustrate one of the manufacturing steps associated with the invention.
Figure 4:
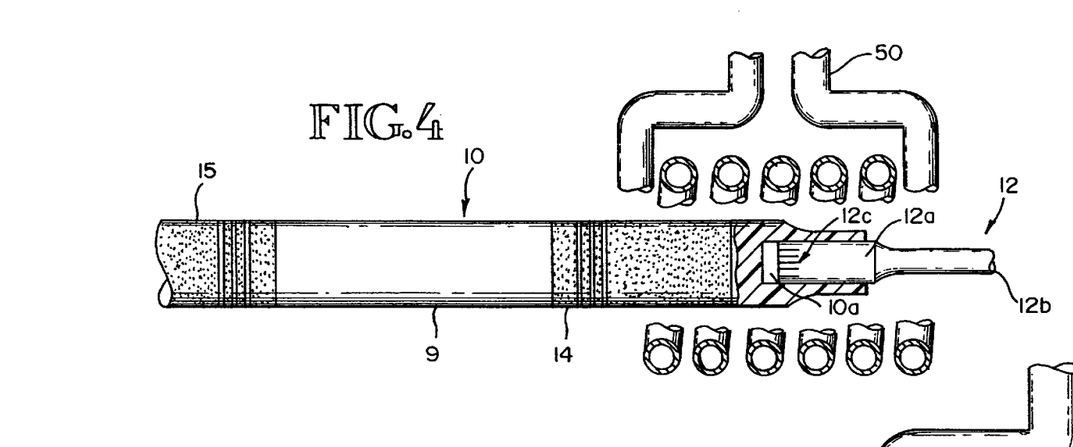
FIG. 4 is an enlarged view of the FIG. 3 instrument inserted into the induction heating coil, with a portion of the coil broken away and a portion of the right end of the handle shown in cross section to illustrate the joint between the handle and the working tip.

The axial bores 10a, 10b are drilled out when the handle is machined; or are provided as elongated cavities when the handle is molded. In either type of manufacture, the bores 10a, 10b are provided with a longitudinal length slightly longer than the length of shank end 12a, 13a that is to be inserted into its respective bore. Consequently, the shank end can be inserted to a predetermined depth, such as ½ inch, with a small cavity left between the butt of the shank end and the end of the bore, as seen in FIGS. 3 and 4, for example. The shank end may be press-fitted into the bore using a pneumatic, mechanical, or hydraulic press with appropriate controls to align the working tip with the handle and to limit the depth of tip insertion to a predetermined amount.

Because of the tight fit between the handle working end bore 10a, 10b and the shank end 12a, 13a, the shank insertion process, preferably a press-fit process, will cause substantial stress in the handle around the bore. This stress will be particularly severe in the region of the handle transition shoulder 16, 17 because that reduced diameter region of the handle will be least capable of enduring those stresses. Unless relieved, this stress has the potential to cause the handle to fracture. In order to relieve those stresses, and also to seal the handle material around the shank end, the handle and working tip combination is subjected to a heat treatment that will cause those stresses to be relieved and that will cause the thermoset plastic around the shank end to seal the scoring marks left in the bore by the press-fitting operation. The preferred means of heat treating the handle and working tip combination is induction heating. After the instrument has been assembled and induction heated, the entire instrument may be annealed by being placed in a baking oven under suitable annealing conditions as hereinafter described.

Figure 5:
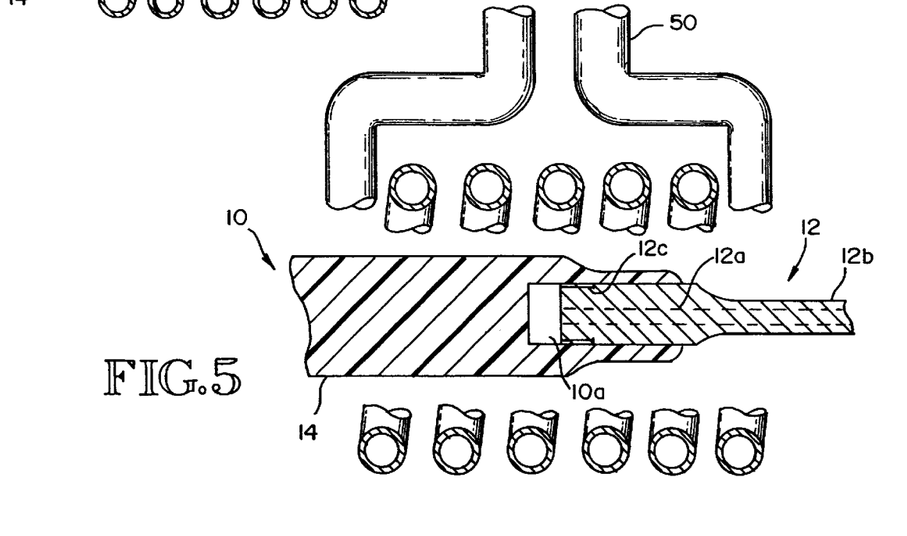
FIG. 5 is a further enlarged view of the FIG. 3 instrument, similar to FIG. 4 but still further enlarged to illustrate the affect of the induction heating step of FIG. 3.

As seen if FIGS. 3–5, the portion of the handle containing the working tip is inserted into an induction heating coil 50 of an induction heating generator 60 so that the bore 10a and the shank end 12a are located in the field of the induction heating coil 50. The handle and working tip combination will be left in the induction heating coil field until heat induced in the stainless steel working tip is sufficient to melt the thermoplastic material surrounding the shank end. Consequently, the thermoplastic material immediately adjacent the shank end will flow to fill the score marks in the bore side wall and embed the adjacent non slip surface 12c into the plastic material of the handle. When the plastic material is softened to the point of filling the score marks in the bore side wall and embedding the non slip surface in the handle, the working tip will be sealed in solid-to-solid contact with the handle and the stresses will be completely relieved within the handle that had been caused by the shank end insertion process. As a consequence of the induction heating process, and its resultant affects on the plastic material surrounding the working tip, the working tip will protrude from the handle as an integral part thereof, with no cracks, holes, grooves or crevices between them that could harbor bacteria or other pathogens.

For any given induction heating system, the timing of the induction heating process only takes that amount of time to accomplish the desired results and no longer. If the induction heating process heats the metal working tip to too great a temperature, or applies the induced heat for too long a period at a reduced temperature, the plastic material in the region of the working tip may be heated too much—to the point where the handle may become deformed. For any given system, a simple trial run can determine the induction heating parameters that are sufficient to accomplish the desired results.

As an example, a Lepel High-Frequency Induction Heating Generator, with a 450,000 Kilohertz output, manufactured by the Lepel Corporation of Edgewood, N.Y., may be used to precisely melt the thermoplastic material of the handle immediately surrounding the working tip to both relieve internal stress and to eliminate working tip assembly scoring. Several assembled instruments could be inserted together in a helical copper induction coil measuring 1¼ inches around and 1 inch long for three seconds to accomplish the desired heating. For instruments having two working tips, the instruments would then be reversed to place the other tips in the field of the induction coil. Other coil configurations and sizes could be employed, with appropriate adjustment of the time interval for the induction heating. The dashed lines through the working tip in FIG. 5 illustrate the depth to which the shank end is heated by hysteresis and eddy currents generated by the induction heating process. The heated area conducts heat into the adjacent plastic material so as to effect a melting of the adjacent plastic material.

Sulfone polymers have been found to be especially suitable for the handle of this invention. Sulfone polymers are amorphous thermosetting thermoplastics. In particular, polyphenylsulfone formulated by Amoco Performance Products, Inc. under the brand name RADEL R has been found to be especially suitable. Other suitable sulfone polymers are polyethersulfone formulated by Amoco Performance Products, Inc. under the brand name RADEL A, and polysulfone formulated by Amoco Performance Products, Inc. under the brand name UDEL. These sulfone polymers, and particularly RADEL R polyphenylsulfone, are high temperature thermosetting polymers that exhibit good thermal stability, toughness, chemical resistance, and stress cracking resistance. They are suitable for use in instruments that are to be sterilized by steam autoclaving, or harsh disinfecting chemicals. Utilizing resin products of the type described in multiple step manufacturing processes results in stress factors in the material of the final product which are not visually detectable but give rise to premature material fatigue and ultimate cracking or failure. For instance, nearly every operation on the plastic material such as machining e.g. knurling or boring, molding, extruding, polishing, and threading all create a certain amount of internal stress in the material of the handle during manufacture. In order to create a durable and safe working instrument, the process step of annealing the final hand instrument product becomes critical. The annealing process step can usually be performed in an annealing oven where the total instrument is subjected to heat for an extended period of time. A satisfactory annealing procedure for the present instrument is oven annealing at a temperature of 380° F over a four hour period. With this treatment, the hand held instrument is free from stress cracking and safe to be sterilized by steam auto-claving or any other treatment to which instruments of this type are normally subjected.

The gripping surface 14 and 15 are knurls that may be machined into the surface of the handle 10. A suitable knurl may be machined into the surface using a 0.096 inch diametral pitched straddle knurler that rides over the rod stock from which handle 10 is formed. A suitable knurl length is approximately 1 to 1⅜ inches. After the knurl is formed for each surface 14, 15, the knurl may be machined to produce identity rings as seen in FIGS. 1 and 2.

Figure 6:
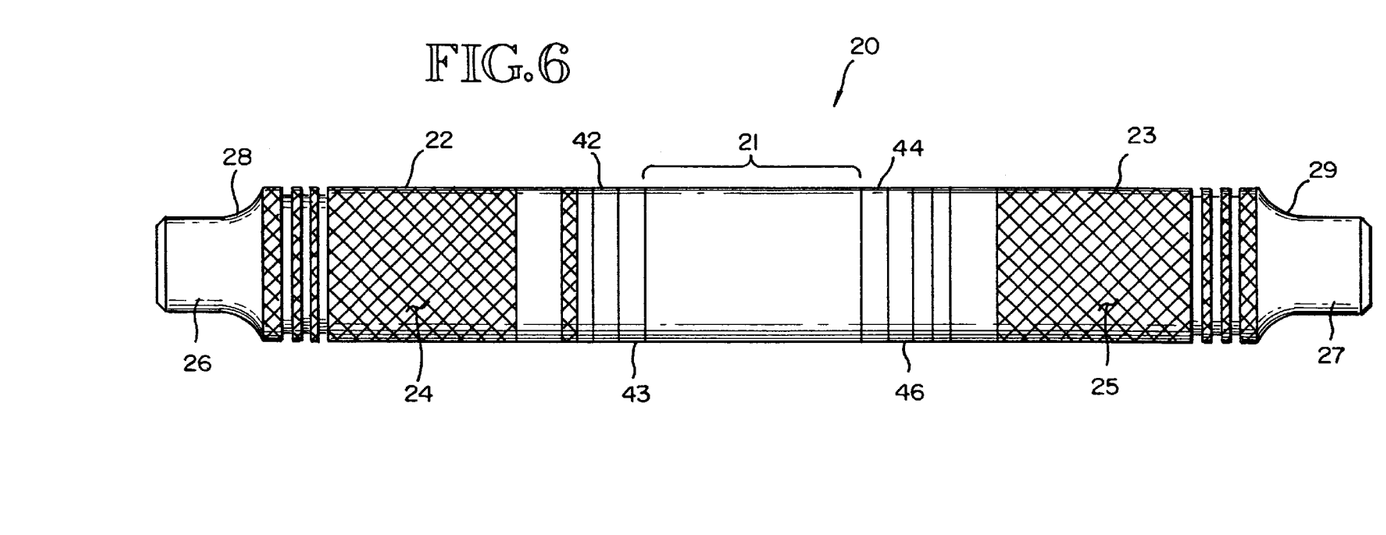
FIG. 6 is a side view of a double ended replaceable tip dental hand instrument in accordance with the invention.
Figure 7:
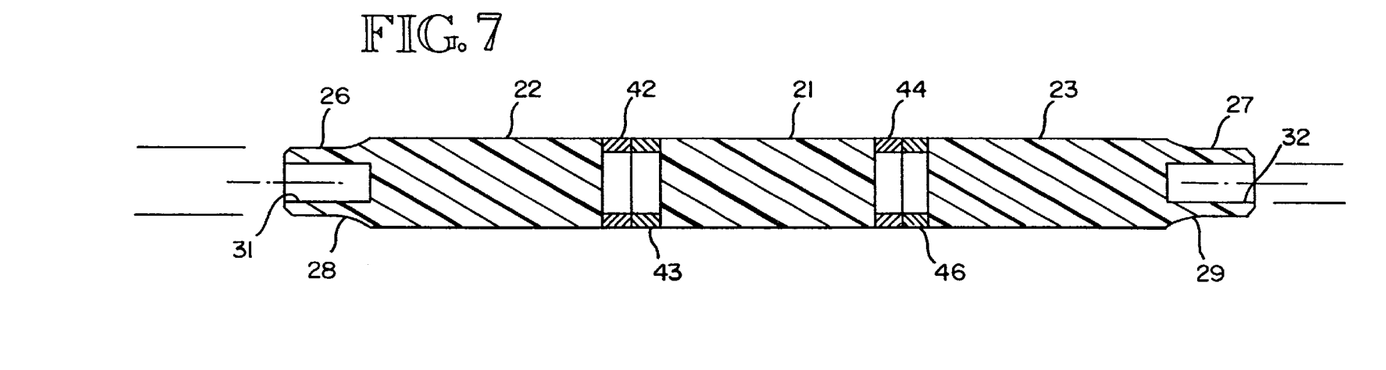
FIG. 7 is a longitudinal cross section of the FIG. 6 instrument in the assembled position.
Figure 8:
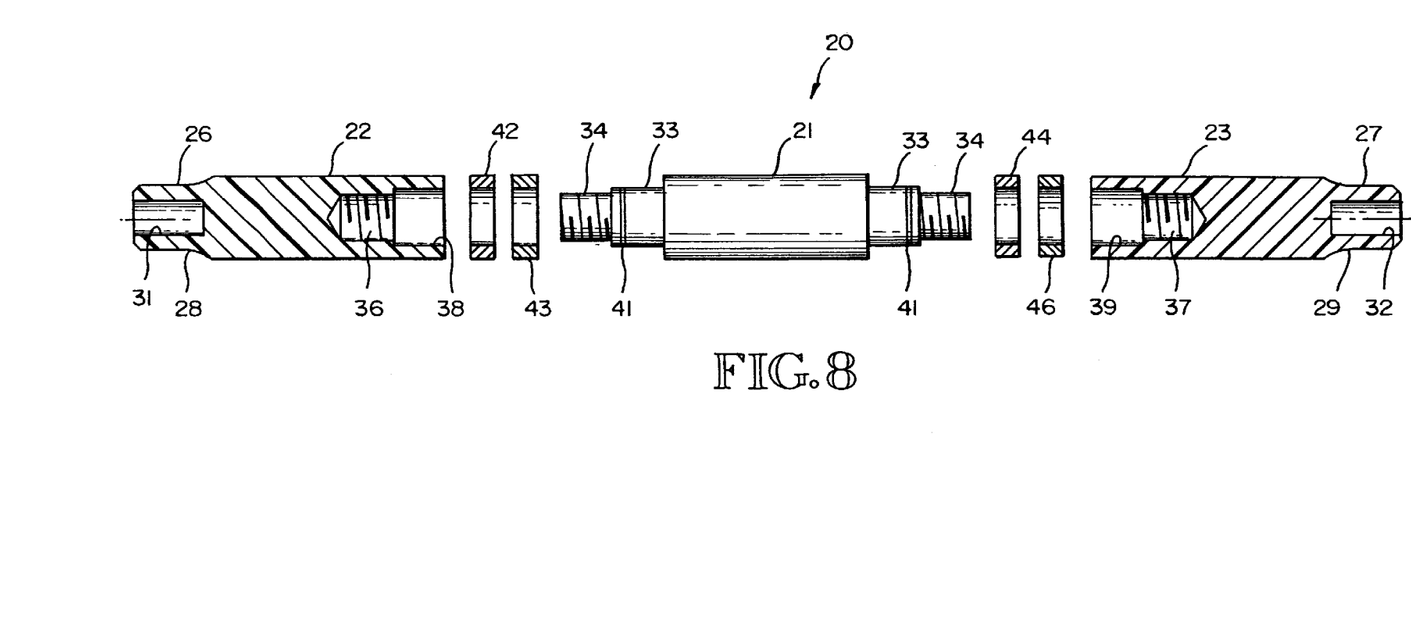
FIG. 8 in an exploded view of the multiple piece handle of FIGS. 6 and 7.

FIGS. 6–8 illustrate a second embodiment of an elongated dental instrument handle. It will be understood that the description of the type of materials utilized and the various manufacturing steps described relative to the FIGS. 1–5 embodiment will also apply to the embodiment shown in FIGS. 6-8. Likewise, it will be understood that the working tips may be inserted into the handle sections to be described using the same press fit and induction heating procedures described in the FIGS. 1–5 embodiment.

Referring to the assembled handle in FIGS. 6 and 7, it will be seen that the handle 20 is made up of three separate sections including the center or base section 21 and opposite working tip end sections 22 and 23 respectively. While the illustrated embodiment is designed as a double-ended instrument to include removable working tips on opposite ends of the instrument, it will be understood that the replaceable tip concept described is equally applicable to a single tip instrument such as shown in FIG. 1 wherein the main body portion 21 would comprise an extended handle such as shown at 9 in FIG. 1. It will also be understood that the material from which the sections 21–23 are constructed is that described previously for the FIGS. 1–5 embodiment. The sections 22 and 23 include finger griping exterior surfaces such as previously described and shown at 24 and 25 respectively of the FIG. 6 embodiment. This surface treatment may be done in the manner previously described to produce the desirable effect. Each of the tip end sections 22 and 23 are provided with working tip receiving terminal ends 26 and 27 respectively for receiving suitable working tips (not shown). As shown in FIGS. 7 and 8, each terminal end 26 and 27 is provided with a bore as shown in 31 and 32 designed as previously explained for the reception of the shank end of a working tip.

The cylindrical center or base section 21 is provided with opposite terminal ends which include a reduced diameter section 33 and a threaded terminal end 34. The terminal ends 34 are designed to engage threaded bores 36 and 37 in the inner ends of the end sections 22 and 23 respectively. Likewise, the reduced diameter shaft portion 33 of the center section 21 is received in the enlarged diameter bores 38 and 39 in the inner ends of the respective end sections 22 and 23. Each reduced diameter section 33 is provided with an O-ring groove for mounting the O-rings 41. The O-rings serve as a barrier to prevent debris and pathogens from entering the threaded areas. With this arrangement, the tip end sections are independently replaceable and may be disposable when replacing worn or broken points as needed without losing the benefit of the remaining serviceability of the opposing point as in standard double-ended instruments. The independently exchangeable tips also allow the users to mix and match any combination of points desired to best fit individual requirements.

In addition to the advantages discussed, the instrument handle assembly may be provided with one or more in-line identification rings 42, 43, 44 and 46 which may be seated on the reduced diameter portions 33 of the central section 21. The ring surfaces may be flush with the handle surface at each end for longer wear and better sterilization than externally applied silicone rings, commonly used in the industry. Such external rings can inhibit tactile grip, harbor pathogens, and break easily with heat sterilization. The rings 42–46 may be color coded or otherwise contain indicia relevant to the identification of the working points. The identification rings will be sized, of course, to be carried on the reduced diameter portions 33 of the center section 21 while allowing engagement of the O-ring seals 41 with the inside interior surface of the bore 38.

Although the present embodiment has been described relative to the use of plastic handles and permanently attached working tips, the basic multiple sectioned handle concept could also be applied to handles constructed of other materials such as metals and metal alloys.

While the preferred embodiments of the invention have been described herein, variations in the design may be made. Because the working tips are inserted after the handles have been manufactured, the handles sans workings tips can be inventoried; with desired working tips inserted as some later time as required to meet demand. Consequently, an extensive inventory of completed instruments is not required, thereby making for a more efficient production and inventory system. Likewise the various sections and identification rings of the multiple piece handle are interchangeable and may be inventoried for selective replacement. The scope of the invention, therefore, is only to be limited by the claims appended hereto.

The embodiments of the invention in which an exclusive property is claimed are defined as follows:

What is claimed is:

1. A dental hand instrument comprising;

an elongated handle formed of a thermosetting plastic, a metal working tip inserted into one end of said handle, said handle having a bore provided in said one end adapted to initially accommodate a shank end of said tip under stress conditions, said shank end including a scored circumferential surface area adjacent the terminal end thereof within said bore, said scored surface being embedded into said handle by flow of the plastic material thereof into the scored surface to form a mechanical non slip connection therebetween to prevent said tip from turning during use, the thermosetting plastic material immediately adjacent said bore being bonded to said shank end free from internal stress forces, said handle and tip being subjected to heat treatment to partially melt at least the surface portion of the thermosetting plastic immediately adjacent the surface of said shank end so as to firmly secure said tip in said handle, to bind said shank end in solid plastic-to-metal contact along said shank end, and to relieve internal stress forces within the plastic material of said handle.

2. The instrument of claim 1 wherein;

said elongated handle includes opposite ends adapted to accommodate a shank end of a metal working tip, each said opposite ends including one said bores, and one said working tips inserted in each said bores and bonded thereto respectively.

3. The instrument of claim 1 including;

a transition shoulder on said handle adjacent said working tip and, a knurled finger gripping surface on said handle adjacent said transition shoulder, said transition shoulder and said gripping surface being constructed and arranged so that said transition shoulder is positioned between and immediately adjacent said tip and said gripping surface.

4. The instrument of claim 3 wherein;

said elongated handle includes opposite ends adapted to accommodate a shank end of a metal working tip, each said opposite ends including one said bores, and one said working tips inserted in each said bores and bonded thereto respectively.

5. A method of manufacturing a dental hand instrument comprising the steps of;

forming an elongated handle from a thermosetting plastic with a bore of a given diameter in one butt end of said handle, inserting the shank end of a metal steel working tip into said bore, said shank end having a diameter slightly larger than said bore whereby the insertion of said shank end creates stress within said thermosetting plastic, heat treating said instrument to relieve the stress created within said thermosetting plastic as a result of inserting said shank end, and melting said thermosetting plastic adjacent said shank end so as to firmly secure said tip in said handle and to bind said shank end in solid plastic-to-metal contact along said shank end.

6. The method of claim 5 wherein said heat treating is accomplished by high frequency induction heating so as to induce heat into the body of said tip to thereby cause the adjacent thermosetting plastic in the walls of said bore to melt and flow around said shank end.

7. A method of joining a metal working tip to a plastic handle comprising the steps of;

forming a cavity of a given diameter in the surface of the handle, scoring the circumferential surface of at least a portion of the shank end of a metal tip having a diameter slightly greater than the diameter of said bore, applying a stress to the plastic walls of said cavity by forcing said shank end therein, scoring the surface of said cavity by passing said scored shank end thereover, and then relieving the stress in the walls of said cavity by application of heat, and bonding the surfaces of said shank end and said cavity together in solid plastic-to-metal contact by application of heat to the body of said shank so as to melt the scored plastic surface, whereby the plastic material immediately adjacent the shank end surface will flow to fill the score marks in the cavity walls and the adjacent scored surface of the shank end will be embedded into the plastic material of the handle to form a mechanical non slip connection and permanent bond.

8. The method of claim 7 including the step of;

inducing heat to said handle and into the body of said metal tip by high frequency induction to relieve stress in the plastic walls of said cavity and to melt the plastic adjacent the surface of said shank end.

9. The method of claim 8 including the step of;

forming said handle from thermosetting plastic material having an elongated body with a finger rest transition region of reduced cross section immediately adjacent one butt end thereof, and forming said cavity in the face of said one butt end.

10. The method of claim 9 wherein the scored portion of said shank end comprises protrusions beyond the surface of said shank end in the order of approximately 0.004 inches plus or minus 0.001 inches to form a non slip surface and the diameter of said cavity is in the order of about 0.002 inches less than the diameter of the shank end.

11. The method of claim 10 including the step of;
forming said handle from a sulfone polymer.

12. The method of claim 11 including the step of; forming said handle by machining from rod stock, and forming said cavity by boring in said one butt end to a depth slightly greater than the length of said shank end,
whereby said shank end may be inserted to a given predetermined depth.

13. The method of claim 11 including the step of;
forming said handle by injection molding to include said cavity in said one butt end, said cavity having a depth slightly greater than the length of said shank end,
whereby said shank end may be inserted to a given predetermined depth.

14. The method of claim 8 including the step of annealing the entire completed instrument at a temperature and period of time sufficient to relieve the stress forces in said thermosetting material induced by manufacturing steps.

15. The method of claim 14 wherein said annealing step is carried out in an annealing oven at a temperature of approximately 280° F. for approximately four hours.

16. The method of claim 9 including the step of annealing the entire completed instrument at a temperature and period of time sufficient to relieve the stress forces in said thermosetting material induced by manufacturing steps.

17. The method of claim 16 wherein said annealing step is carried out in an annealing oven at a temperature of approximately 280° F. for approximately four hours.

18. A dental hand instrument comprising in combination;
a plastic handle having an elongated body including a butt end,
means defining a cavity of a given diameter in the face of said one butt end,
a metal working tip including a shank end thereon located in said cavity,
said shank end having a non slip surface located within said cavity,
the initial diameter of said cavity being slightly less than the diameter of said shank end, whereby the plastic material adjacent said cavity is initially stressed and said non slip surface roughens the inside surface of said cavity during insertion, and
the initial stress in said plastic material being relieved by heat treatment thereto following insertion of the shank end,
said heat treatment serving to melt the plastic immediately adjacent the surface of said shank end to embed said scored area into the plastic handle to form a mechanical connection and to bond said roughened surface of the cavity to the shank surface to form a solid plastic-to-metal bond.

19. The combination of claim 18 wherein;
said non slip surface comprises a circumferential surface scored area adjacent the terminal portion of said shank, said scored area serving to roughen the inside surface of said cavity during insertion of the shank end,
whereby melting of said plastic immediately adjacent the surface of said shank is enhanced and plastic-to-metal bonding is facilitated.

20. The combination of claim 19 wherein;
said elongated body includes a finger rest transition portion of reduced cross sectional area immediately adjacent said one butt end,
said heat treatment eliminating stress in the reduced cross sectional area of said finger rest.

21. A dental hand instrument comprising;
an elongated handle formed of a thermosetting plastic with a cavity of a given diameter located in an end thereof,
a metal working tip having a shank end with a non slip surface and having a diameter slightly greater than said cavity,
said shank end having a press fit in said cavity, and
a heat bond between the surface of said cavity and said shank end,
the non slip surface being embedded into the thermosetting plastic and said plastic being free of internal stress forces,
whereby a solid plastic-to-metal bond and seal is formed between said shank and the cavity walls.

22. A dental hand instrument comprising;
a cylindrical base handle section and a working tip section, both said sections being formed of a thermosetting plastic with a releasable connection therebetween for removably connecting said sections,
said working tip section including a terminal end with a cavity of a given diameter therein,
a metal working tip having a shank end with a non slip surface and having a diameter slightly greater than said cavity,
said shank end having a press fit in said cavity, and
a heat bond between the surface of said cavity and said shank end,
the non slip surface being embedded into the thermosetting plastic and said plastic being free of internal stress forces,
whereby a solid plastic-to-metal bond and seal is formed between said shank and the cavity walls and said working tip section is replaceable.

23. The instrument of claim 22 wherein said releasable connection comprises a screw threaded connection.

24. The instrument of claim 22 wherein said working tip section comprises a first working tip section connected to one end of said base handle section, said instrument including;
a second working tip section with a releasable connection to the other end of said base handle section,
said second working tip section and releasable connection being identical and interchangeable with said first working tip section.

25. The instrument of claim 24, wherein said releasable connection comprises a screw threaded connection.

26. The instrument of claim 25 wherein said screw threaded connections each comprise;
a reduced diameter end portion on said base handle section having a screw threaded terminal end, and
said working tip sections having a bore in the end thereof opposite said cavity for receiving said reduced diameter end portion of the base handle section with screw threads therein for engaging the screw threaded terminal end of the reduced diameter end portion, and
O-ring sealing means carried by said reduced diameter base handle section and said working tip section.

27. The instrument of claim 26 including;
at least one identification ring removably carried on said reduced diameter portion to be clamped between said base handle and working tip sections, said identification ring having the outer cylindrical surface thereof flush with the surfaces of said base handle and working tip sections.

28. A dental hand instrument comprising;

a cylindrical base handle section and a working tip section; both said sections being formed with a releasable connection therebetween for removably connecting said sections, said working tip section comprising a thermosetting plastic and including a terminal end mounting a metal working tip connected thereto with a solid plastic-to-metal bond.

29. The instrument of claim 28 wherein said working tip section comprises a first working tip section connected to one end of said base handle section, said instrument including;

a second working tip section with a releasable connection to the other end of said base handle section, said second working tip section and releasable connection being identical and interchangeable with said first working tip section.

30. A dental hand instrument comprising;

a cylindrical base handle section and a working tip section; both said sections comprising a thermosetting plastic and formed with a releasable connection therebetween for removably collecting said sections, said working tip section including a terminal end mounting a metal working tip connected thereto with a solid plastic-to-metal bond.

31. The instrument of claim 30 wherein said releasable connection comprises a screw threaded-connection.

32. The instrument of claim 30 wherein said working tip section comprises a first working tip-section connected to one end of said base handle section, said instrument including;

a second working tip section with a releasable connection to the other end of said base handle section, said second working tip section and releasable connection being identical and interchangeable with said first working tip section.

33. The instrument of claim 32 wherein said releasable connection comprises a screw threaded connection.

34. The instrument of claim 33 wherein said screw threaded connections each comprises;

a reduced diameter end portion on said base handle section having a screw threaded terminal end, and said working tip sections having a bore in the end thereof opposite said cavity for receiving said reduced diameter end portion of the base handle section with screw threads therein for engaging the screw threaded terminal end of the reduced diameter end portion, and O-ring sealing means carried by said reduced diameter base handle section and said working tip section.

35. The instrument of claim 34 including;

at least one identification ring removably carried on said reduced diameter portion to be clamped between said base handel and working tip sections, said identification ring having the outer cylindrical surface thereof flush with the surfaces of said base handle and working tip sections.

* * * * *

UNITED STATES PATENT AND TRADEMARK OFFICE
CERTIFICATE OF CORRECTION

PATENT NO. : 6,257,887 B1
DATED : July 10, 2001
INVENTOR(S) : Brad B. Heckerman; Russ Jenkins; Dennis Meuchels; Jeff Smithers It is certified that error appears in the above-identified patent and that said Letters Patent is hereby corrected as shown below:

<u>Column 11,</u>
Line 27, change "collecting" to -- connecting --.

Signed and Sealed this

Twenty-ninth Day of January, 2002

Attest:

Attesting Officer

JAMES E. ROGAN
*Director of the United States Patent and Trademark Office*